(12) United States Patent
Hoffman et al.

(10) Patent No.: US 8,512,344 B2
(45) Date of Patent: Aug. 20, 2013

(54) INSERTION INSTRUMENT FOR A SPINAL FIXATION SYSTEM

(75) Inventors: Jeffrey A. Hoffman, Marquette, MI (US); Gregory A. Berrevoets, Skandia, MI (US); Michael D. Kakuk, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 662 days.

(21) Appl. No.: 12/423,786

(22) Filed: Apr. 14, 2009

(65) Prior Publication Data
US 2009/0234395 A1 Sep. 17, 2009

Related U.S. Application Data

(63) Continuation-in-part of application No. 11/839,843, filed on Aug. 16, 2007.

(60) Provisional application No. 61/044,585, filed on Apr. 14, 2008, provisional application No. 60/822,603, filed on Aug. 16, 2006.

(51) Int. Cl.
*A61B 17/70* (2006.01)

(52) U.S. Cl.
USPC ............................................. 606/86 A

(58) Field of Classification Search
USPC ............. 606/86 A, 86 R, 279, 79–80, 99; 81/451–455
See application file for complete search history.

(56) References Cited

U.S. PATENT DOCUMENTS

| | | | | |
|---|---|---|---|---|
| 203,581 A * | 5/1878 | Birch | | 81/112 |
| 1,912,317 A * | 5/1933 | Stewart | | 81/455 |
| 3,753,454 A * | 8/1973 | Totsu | | 81/448 |
| 4,363,250 A * | 12/1982 | Suga | | 81/455 |
| 4,759,241 A * | 7/1988 | Voswinkel | | 81/453 |
| 5,364,397 A * | 11/1994 | Hayes et al. | | 606/86 A |
| 5,720,751 A * | 2/1998 | Jackson | | 606/86 R |
| 6,746,451 B2 * | 6/2004 | Middleton et al. | | 606/79 |
| 6,805,716 B2 * | 10/2004 | Ralph et al. | | 623/17.16 |
| 7,243,688 B2 * | 7/2007 | Stark | | 140/147 |
| 2002/0099377 A1 * | 7/2002 | Zucherman et al. | | 606/61 |
| 2004/0267275 A1 * | 12/2004 | Cournoyer et al. | | 606/99 |
| 2005/0090824 A1 * | 4/2005 | Shluzas et al. | | 606/61 |
| 2005/0277934 A1 * | 12/2005 | Vardiman | | 606/61 |
| 2006/0200132 A1 * | 9/2006 | Chao et al. | | 606/61 |
| 2007/0162010 A1 * | 7/2007 | Chao et al. | | 606/61 |
| 2008/0045955 A1 | 2/2008 | Berrevoets et al. | | |
| 2009/0163963 A1 | 6/2009 | Berrevoets | | |

* cited by examiner

*Primary Examiner* — Jan Christopher Merene
*Assistant Examiner* — Steven Cotroneo
(74) *Attorney, Agent, or Firm* — Fitch, Even, Tabin & Flannery LLP (57) ABSTRACT

A medical instrument apparatus and method is provided to insert and release medical implants. This invention pertains generally to medical instruments and more specifically to spinal implant insertion instruments for spinal fixation systems. The insertion instrument may provide a positive locking and unlocking actuator, preferably in the form of a lever, which ensures that the pedicle screw and yoke assembly is either mechanically locked to the insertion instrument or unlocked to the insertion instrument. The positive locking and unlocking actuator of the insertion instrument eliminates guesswork for the surgeon because the surgeon can readily know if the pedicle screw and yoke assembly is attached to the insertion instrument or not. Superelastic components may also be included to shift components in a first direction and pull components under superelastic tension in a second direction for increased holding force.

6 Claims, 11 Drawing Sheets

INSERTION INSTRUMENT FOR A SPINAL FIXATION SYSTEM

This application claims the benefit of U.S. Provisional Application No. 61/044,585, filed Apr. 14, 2008, and is a continuation-in-part of U.S. Utility patent application Ser. No. 11/839,843, filed Aug. 16, 2007, which claims the benefit of U.S. Provisional Application No. 60/822,603, filed Aug. 16, 2006, all of which are hereby incorporated herein by reference as if fully set forth herein.

BACKGROUND OF THE INVENTION

This invention pertains generally to medical instruments and more specifically to spinal implant insertion instruments for spinal fixation systems. Spinal rods or other stabilization devices for partially or fully immobilizing vertebral bones of the spinal column are typically anchored to the vertebrae via anchor members such as bone screws or hooks. The rods are connected to the anchor members by generally yoke-shaped coupling members that can be integral with or coupled to the anchor member the coupling members may be formed as separate components from the anchor member so that the anchor may pivot with respect to the coupling member. Generally these systems employ a compression or lock member (such as a threaded or non-threaded cap secured to the coupling member) that secures an elongate stabilization device, such as a spinal rod, within the coupling member.

Examples of coupling devices are disclosed in U.S. Utility patent application Ser. No. 11/839,843 and Provisional Applications 60/822,603 and 60/825,366, which disclose several different exemplary devices, especially pedicle screw devices and systems. These systems must be secured to bone using an anchor member, preferably a threaded shank forming a screw for rotatable insertion into the bone. These devices are commonly screwed into the pedicle region of a vertebra in order to secure a spinal rod or other stabilization member thereto. There remains a need, however, to provide improved tools for securing those systems to the spine.

SUMMARY OF THE INVENTION

The systems disclosed herein include instruments for implanting one or more anchor devices for securing an elongate stabilization member to the vertebrae. The anchor devices have a coupling member or yoke and an anchor member. For instance, the yoke and anchor may form a pedicle screw assembly to be implanted in the pedicle region of a vertebrae. The discussion below will focus on pedicle screw devices, although other anchor devices may alternatively be used with the instruments discussed herein. No matter whether the yoke and screw portions are integral or separate, the screw must be driven into a vertebra with the yoke coupled thereto. In order to stabilize the yoke and screw of the device to facilitate rotatably driving or screwing of the device into bone, an instrument is provided to engage both the anchor and yoke and allow rotation thereof to rotatably drive the anchor into the surface of the bone. The instrument exerts a holding force to hold the pedicle screw device against the instrument to prevent wandering of the screw and/or yoke under the loads required to affix the pedicle screw device to bone. The insertion instrument is designed to assist the implantation of devices in remote locations and may be configured to fit through narrow openings for use in minimally invasive surgical systems ("MIS" systems).

The inserter tool or instrument secures the yoke of a pedicle screw mechanically to hold the yoke in place relative to the instrument as the instrument secures the pedicle screw and acts to rotate the screw. In order to provide sufficient strength to secure the yoke to the instrument, the mechanism that locks and unlocks the yoke with respect to the instrument preferably has one or more superelastic components that may be tensioned while securing the yoke. The superelastic component(s) allows the amount of force holding the pedicle screw device to the instrument to be significantly increased after the point at which components have been fully shifted to their locked positions. Unlike more rigid materials such as steel, high loads may be placed on superelastic materials without permanent deformation of the components.

The instruments provided herein have a head portion for engaging the pedicle screw device, a grasping or holding mechanism that may quickly and easily secure and release a pedicle screw device to the head portion, and an actuator for causing the holding mechanism to secure and release the pedicle screw device. When the actuator lever is in a "locked" position, it is known that the pedicle screw device is fully secured to the instrument, eliminating guesswork usually involved in securing an implant to an insertion device. Other medical insertion instruments rely primarily on threaded engagement mechanisms (with a threaded instrument tip and threaded interior of the screw head) to lock the implant to the insertion instrument, which can have varying degrees of locking between the insertion instrument and the implant. Such threaded medical instruments do not have a positive lock/unlock state and there is no indication as to the state of attachment of the connected implants. The partial locking of an insertion instrument and an implant can cause mechanical damage to the implant and/or the patient if the operator removes the insertion instrument with partial locking or engagement between the insertion instrument and the implant.

In preferred embodiments, the insertion instrument provides a positive locking and unlocking actuator, preferably in the form of a lever, that ensures that the pedicle screw device is either mechanically locked to the insertion instrument or released from the insertion instrument. The actuator lever of the insertion instrument eliminates guesswork for the surgeon because the surgeon can readily know if the pedicle screw and yoke assembly is attached to the insertion instrument based on whether the lever is positioned in a predetermined "locked" or "holding" position or a predetermined "unlocked" or "release" position. The lever provides a quick and easy method of attaching and detaching a yoke and pedicle screw assembly that provides immediate visual and tactile indication of the state of the attachment of the assembly, and eliminates uncertainty for the surgeon as to whether he or she can remove the insertion instrument from the patient without mechanical interference from the attached pedicle screw and yoke assembly during the urgency of surgery.

In one form, the instrument is provided with a positive lock actuator that biases the lever so that it is either in the locked or unlocked state but does not generally stay in an intermediate position. In this form, the insertion instrument does not generally have varying degrees of locking because an internal mechanism will drive the lever of the instrument to either the on or off state. Only by direct interference by the operator of the device can the insertion instrument remain in a partial lock state.

Another aspect of the present invention is that simplified mechanical operation allows for rugged and reliable operation. A further aspect of the invention is the minimum profile of the device, i.e. the small diameter, which allows a surgeon to only have to make a small incision for implantation and thus reduces trauma and recovery time for the patient. The use of superelastic materials within a rigid outer structure allows for the instrument to have excellent strength in securing the pedicle screw device thereto while maintaining a minimal cross sectional profile.

The instrument provides the surgeon with the ability to drive pedicle screws into vertebrae of the spine by rotation of the insertion instrument with the attached pedicle screw and yoke assemblies. The yoke and screw are held to the instrument with sufficient force to prevent wandering of the screw and/or yoke as the screw is driven into bone. Additional advantages and features of the invention will become apparent from the following description. While the instruments herein may be used with a wide variety of pedicle screw devices and other fixation systems with little or no modification to structure and size, they will be described and illustrated with specific pedicle screw systems. This description is in no way meant to be limiting with respect to the instruments described herein.

DETAILED DESCRIPTION OF THE PREFERRED EMBODIMENT

The devices disclosed herein provide insertion of spinal fixation systems and securing the same to the spinal column of a patient. However, any type of object requiring remote insertion or extraction could utilize the instruments disclosed herein. This invention could provide uses beyond medical instrument devices and be easily incorporated into other mechanical systems for the insertion of parts into inaccessible locations especially in the repair of engines. The insertion device could readily be adapted for use in the automotive or aerospace fields for assembly or repair of automobiles, airplanes, or space craft. The insertion technology may also have domestic or military applications in the home or on the battlefield.

If desired, the entire insertion instrument as well as the pedicle screw and yoke assembly can be cannulated, i.e. containing a hole through the center of the insertion instrument down the entire length of the devices, in order to use a guide wire to direct the location of the implantation. A guide wire typically is inserted to achieve an initial accurate location and the surrounding tissue is distracted. Once the tissue is distracted, the cannulated insertion instrument as well as cannulated pedicle screw and yoke assembly can be slid to the correct implantation location over the guide wire.

The following location and direction convention will be used through drawings and their descriptions. In describing the surgical instrument of the present invention, the term "proximal" refers to a direction of the instrument away from the patient and towards the user while the term "distal" refers to a direction of the instrument towards the patient and away from the user. The "proximal direction" is referring to any motion toward the user. The "distal end" of the insertion instrument secures the implant. The "distal direction" is referring to any motion toward the distal end or toward the patient when the insertion instrument is positioned for operation at the surgical site.

Figure 1:
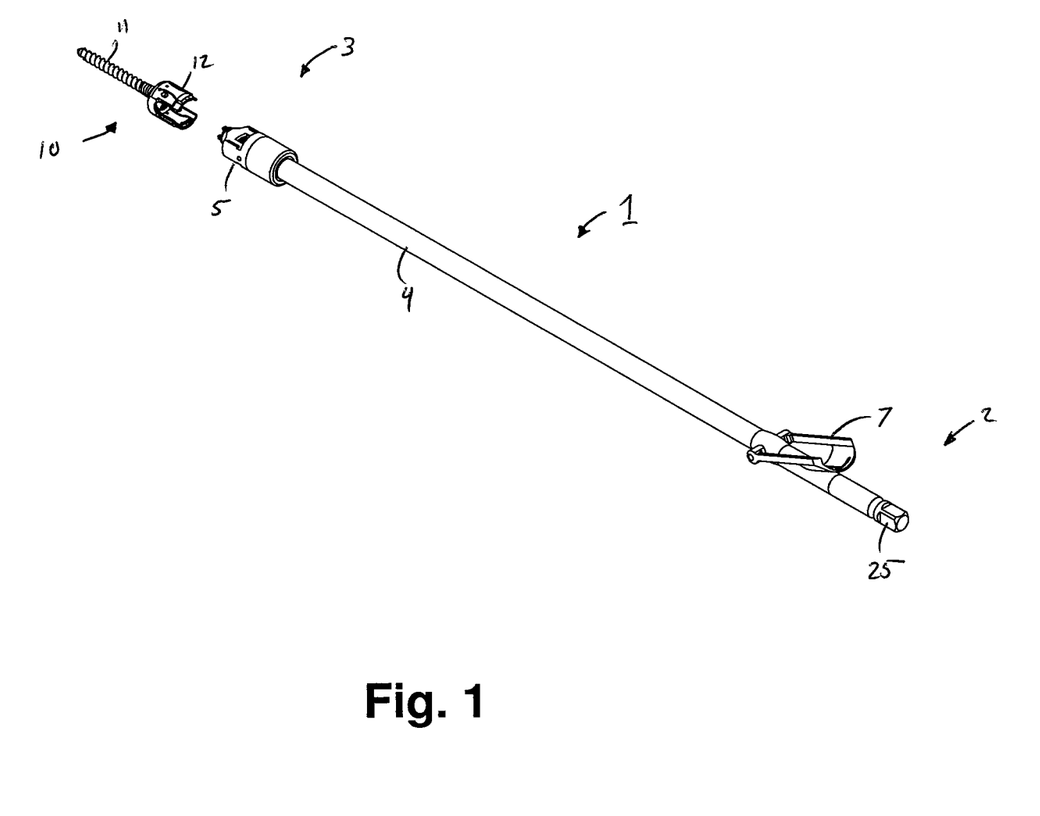
FIG. 1 is a perspective view of one form of insertion instrument in the unlocked position without the coupling member implant attached.

Referring to FIG. 1, the apparatus for inserting implant, i.e. the insertion instrument 1, is shown with a pedicle screw assembly 10 positioned near the distal end toward the left. The pedicle screw assembly 10 has a screw member 11 and a yoke member 12. The instrument 1 includes an elongate tubular shaft 4 with a passage extending therethrough. The operative distal end 3 includes a head portion or holding mechanism 5 configured to retain the yoke and anchor. An actuator lever 7 is used to secure the head portion 5 of the instrument 1 to the pedicle screw device or assembly 11.

The holding mechanism 5 for holding and releasing the screw assembly 11 contains a mechanical system for positive locking and releasing of an implant, and is located at the head portion located at the distal end 3 of the insertion instrument 1. The holding mechanism will be described in detail later in the specification. An actuator lever 7 is also provided to activate the holding mechanism, and is coupled to the shaft 4 by a hinge portion 75 including an off-center actuator pin 71 that rotates about the center of the hinge portion 75. The holding mechanism 5 of the head is connected by a hollow shaft 4 to the positive locking actuator lever 7. The holding mechanism 5 is mechanically and operatively linked to the actuator 7 by mechanical linkages located within the hollow shaft 4, which will be explained below.

The proximal end 2 of the insertion instrument 1 has a polygonal structure 25 for attaching handles or levers for mechanical advantage. The entire insertion instrument 1 will be driven by a rotational force, i.e. torque, with a handle (not shown) to drive the preferred implant of a pedicle screw into the vertebra of a patient. The handle may be detachable or fixed to the elongate shaft 4. In an alternative embodiment, the handle can be attached by any number of cam locking systems. In yet another embodiment, the handle can be attached by providing a threaded surface to screw a handle into instead of a rectangular structure and groove. Finally, the handle itself can have any number of shapes. In the preferred embodiment, the handle is a T-shaped. In an alternative embodiment, the handle can be a knurled knob or lever.

Figure 2:
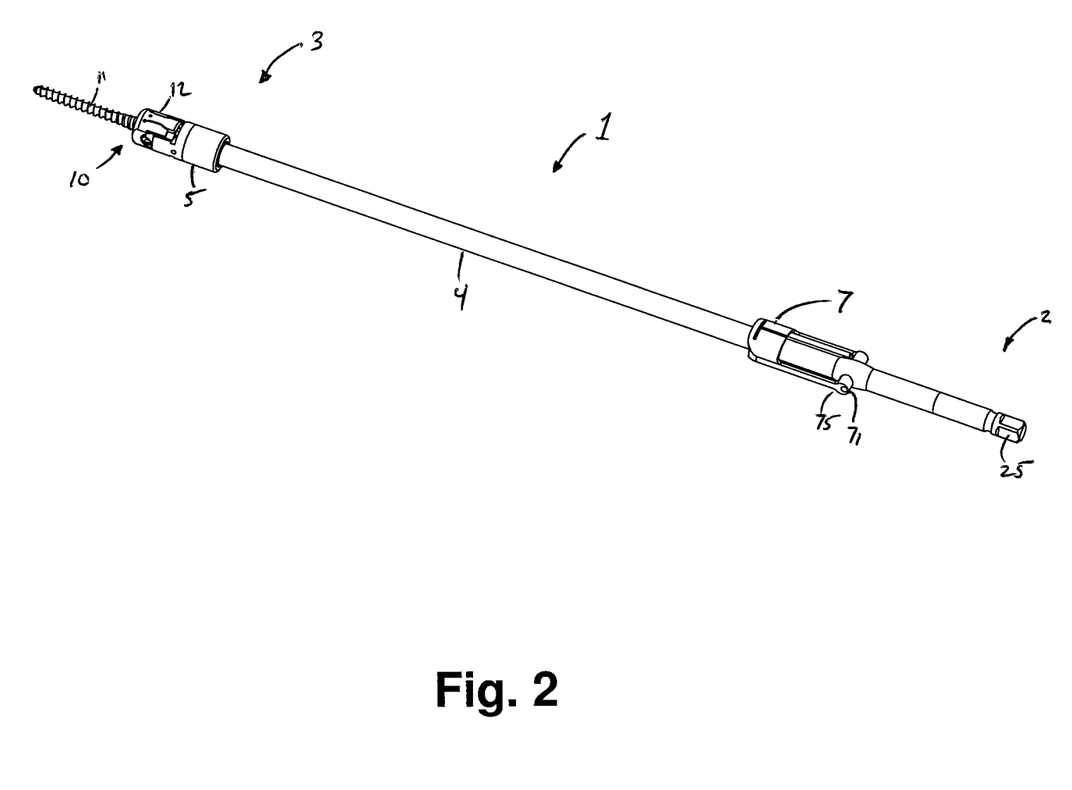
FIG. 2 is a perspective view of an insertion instrument in the locked position and secured to a pedicle screw device.

Referring to FIG. 2, the instrument for inserting pedicle screw devices is shown with the locking actuator 7 in the locked position with the pedicle screw device 10 attached to the instrument head 5. In the preferred embodiment, the insertion instrument 1 has a slender overall exterior profile for the complete assembly to allow insertion through a small incision for minimal invasive surgery from various approaches through the patient's body, although the instrument may be used in open surgeries as well. As shown in FIG. 2, the positive locking actuator 7 may have a cylindrical shape to allow the actuator 7 to rest essentially flush on the surface of the hollow shaft 4. The cylindrical shape of the positive locking actuator 7 also provides an ergonomic shape for operation with the thumb of the user. In an alternative embodiment, the insertion instrument can be curved for an anterior or lateral surgical approach.

Figure 3:
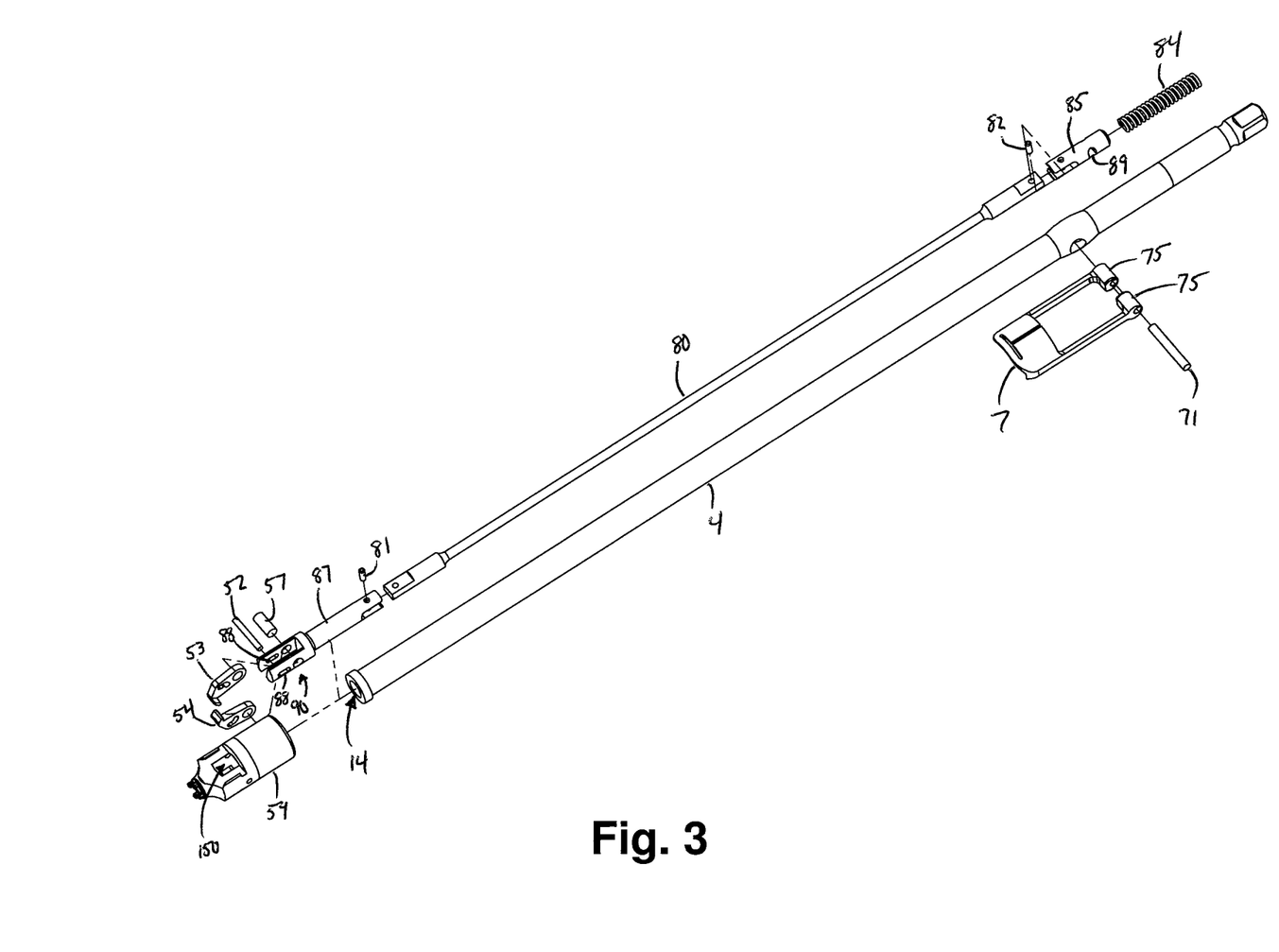
FIG. 3 is an exploded view of an insertion instrument.

The instrument 1 is also shown in an exploded view in FIG. 3. It can be seen in the exploded view that the elongate shaft 4 has a bore 14 through which internal components of the instrument pass. At the proximal end, the pivoting actuator lever 7 is attached to the shaft 4 by hinge portions 75. An actuator pin 71 passes through the hinge portions 75 and is offset from the center of the hinges 75 so that pivoting the lever 7 about the hinges 75 shifts the actuator pin 71 proximally and distally (by generally following the circumference of the hinges 75). The pin 71 also passes through an opening 89 in an actuator shaft portion 85 that is disposed inside the bore 14 of the shaft 4. The actuator shaft 85 is biased toward the distal end of the instrument by a spring 84 also disposed in the bore 14. The actuator shaft 85 is coupled to a superelastic linkage 80, which is in turn coupled to a control shaft 87 that controls the deployment of actuator dogs 53 and 54 configured to grasp and hold the yoke of a pedicle screw device. Pivoting of the actuator lever 7 shifts the off-center actuator pin 71, causing linear travel of the actuator shaft 85, superelastic linkage 80, and control shaft 87 through the bore 14 of the shaft portion 4. The actuator dogs 53 and 54 are pivotably coupled to the control shaft 87. A pivot pin 57 fixes one end of the control shaft 87, and a deployment pin 52 in a fixed position with respect to the shaft 4 and disposed through elongate openings 88 of the control shaft 87. The control shaft 87 is able to travel linearly through the bore 14 of the shaft 4 despite the fixed deployment pin 52 disposed therethrough, because of the elongate shape of the opening opening 88. As the control shaft 87 and the actuator dogs 53 and 54 connected thereto via the pivot pin 57 travel with respect to the deployment pin 52, the deployment pin 52 cams against the actuator dogs 53 and 53, as explained below, to pivot the actuator dogs outward and deploy the ends thereof outward through openings 150 through the housing 59 of the head portion.

Figure 4:
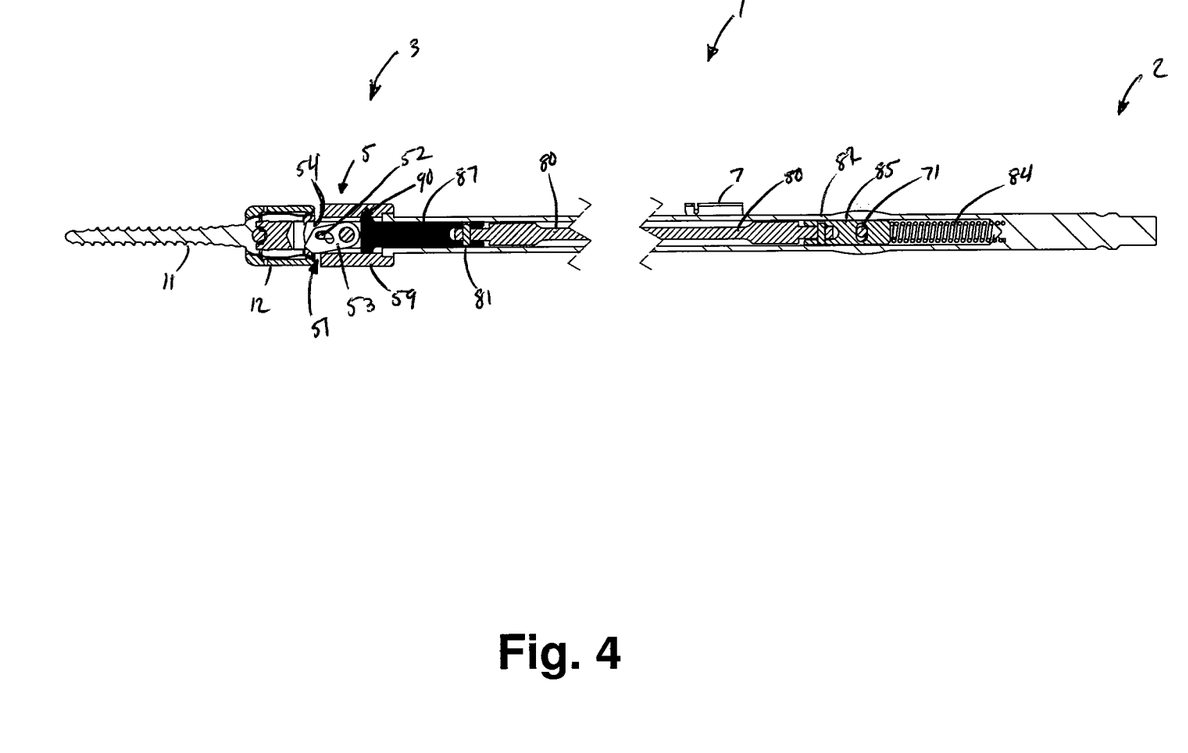
FIG. 4 is a side cross section of an insertion instrument secured and locked to a pedicle screw device.

Referring to FIG. 4, a cross-sectional view of the apparatus for inserting pedicle screw devices is shown with the positive locking actuator 7 in the locked position and the pedicle screw assembly 10 attached to the instrument head portion 5.

In the preferred embodiment, the internal holding assembly 51 within the instrument head portion 5 is mechanically connected to the proximal locking actuator 7 with a superelastic linkage 80 in the form of a rod. The superelastic linkage 80 is preferably made of the resilient material NITINOL which has the property of being a highly elastic metal and of high strength, although other superelastic materials may also be used. NITINOL (an acronym for NIckel TItanium Naval Ordnance Laboratory) is a family of intermetallic materials, which contain a mixture of nickel and titanium. The use of NITINOL provides excellent holding force in the holding mechanism 5 because NITINOL has enough strength to create high levels of tensile force with minimal displacement. For instance, the linkage may be configured to generate 100-200 pounds or more of tensile force to hold a pedicle screw device to the instrument head. The length and diameter of the superelastic portion may be configured to generate a set amount of strain or tensile force, but the desire to increase the holding force of the holding mechanism via the superelastic portion should be balanced against the desire for longevity of the instrument. For instance, the superelastic portion should generally be limited to a strain of about 0.8% or lower in order to last 5 million cycles, but in many applications a greater holding force may desirable. Therefore, the superelastic portion may be configured to achieve 2-3% strain, for example, during use, recognizing that the portion will likely wear out in less than 5 million cycles.

Despite its desirability, NITINOL is very difficult to machine and therefore it is preferred to utilize a simply shaped rod of NITINOL connected to other portions of the actuator device with pins 81 and 82 that keeps the amount of machining of the NITINOL metal to a minimum. Nevertheless, if desired, the entire shaft between the holding mechanism and the actuator may be formed of a superelastic material.

NITINOL is an alloy of nickel and titanium that has superelastic and a shape memory properties. Superelasticity (also referred to as pseudoelasticity) is an elastic (impermanent) response to relatively high stress caused by a phase transformation between the austenitic and martensitic phases of a crystal. A superelastic material returns to its previous shape after the removal of even relatively high applied strains. Above its transformation temperature, NITINOL is superelastic, able to withstand deformation when a load is applied and return to its original shape when the load is removed. Below its transformation temperature, it displays a shape memory effect—when deformed it will remain in that shape until heated above its transformation temperature, at which time it will return to its original shape. The instruments disclosed herein take advantage of the superelastic properties of NITINOL and other superelastic materials. NITINOL is typically composed of approximately 50 to 55.6% nickel by weight, but other ratios may be used. Making small changes in the composition can change the transition temperature of the alloy significantly. For this reason, NITINOL may or may not be superelastic at room temperature, and the composition of the NITINOL or other superelastic material should be designed to behave resiliently under the temperature conditions at which it will be used.

Other shape memory alloys may be used to form the superelastic linkage between the holding mechanism and the actuator mechanism. However, the transition temperature of the alloy should be taken into account to determine if the linkage will be superelastic under the conditions in the operating room in which the instrument is to be used. In addition to NITINOL (NiTi), other shape memory alloys include, but are not limited to, Ag—Cd, Au—Cd, Cu—Al—Ni, Cu—Sn, Cu—Zn—Si/Al/Sn, Fe—Pt, Mn—Cu—Fe—Mn—Si, Co—Ni—Al, Co—Ni—Ga, Ni—Fe—Ga, and Ti—Pd. One of ordinary skill in the art would be able to select relative amounts of metals to form an alloy best suited for particular conditions.

The resilient linkage 80 is connected with a distal pin 81 to the holding mechanism. The distal pin 81 may be made of steel or some other durable and relatively inexpensive component. As explained above with respect to FIG. 3, the holding mechanism 5 includes a control shaft 87 that is shiftable within a housing 59 and deployable actuator dogs 53 and 54 that pivot in opposite directions in response to shifting of the control shaft 87. The control shaft 87 provides a transfer of tensile force to the actuator dogs 53 and 54 through a fixed deployment pin 52. The actuator dogs 53 and 54 mechanically engage a lip of the interior of the pedicle screw yoke 12 when pivoted outward. The dogs 53 and 54 are deployed as the control shaft 87 shifts backward relative to a stationary deployment pin 52. The deployment pin is disposed in slots in the actuator dogs that are configured to shift the pivotable actuator dogs outward as the deployment pin 52 and slot are shifted relative to one another, as explained in connection with FIGS. 6a-c.

Figure 6:
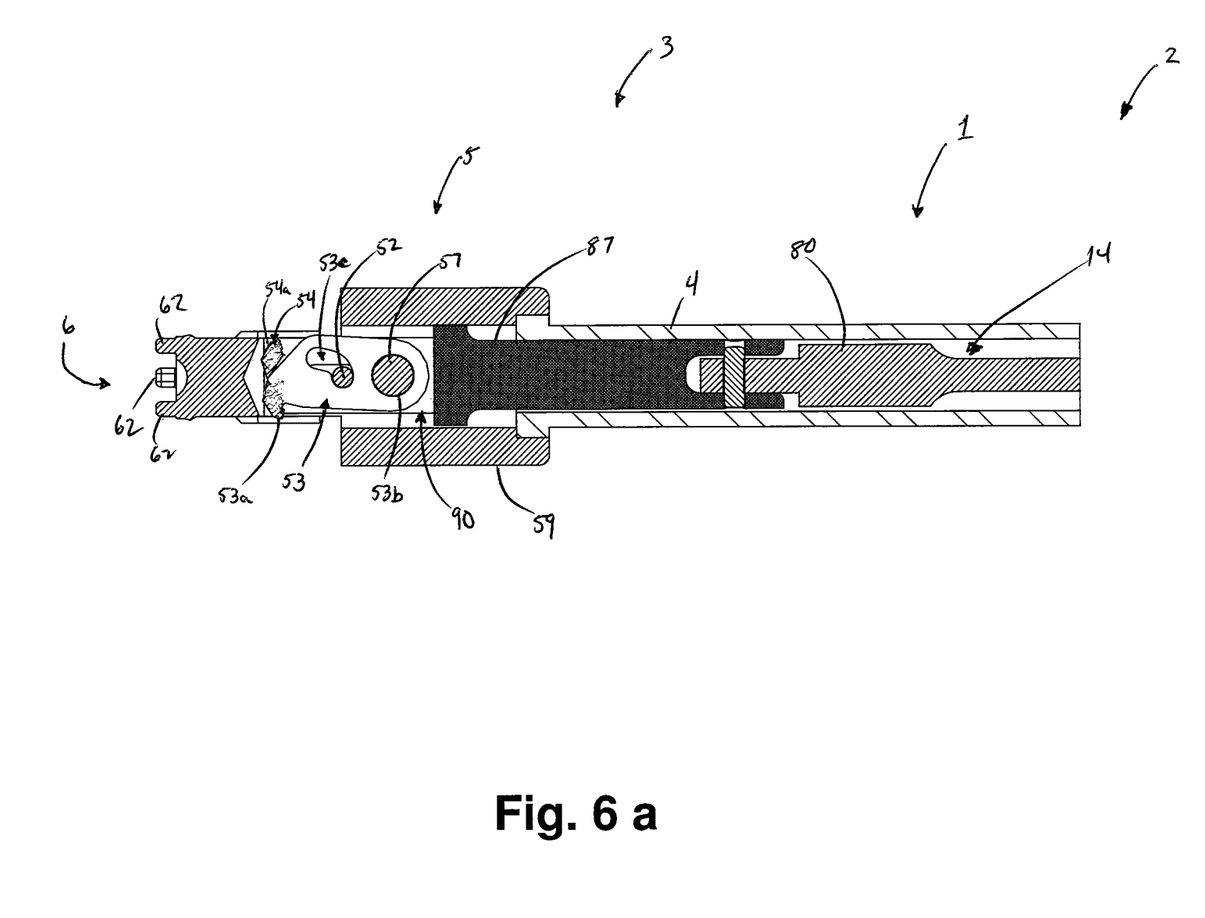
FIG. 6a-6c are partial cross-section views of the holding mechanism of the insertion instrument.
Figure 7:
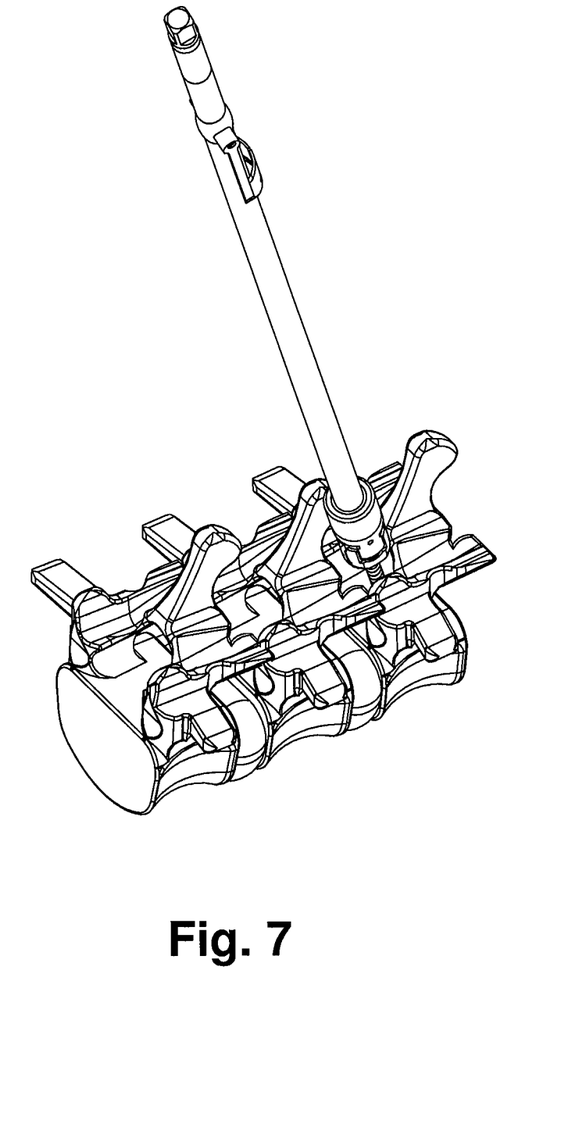
FIG. 7 is a view of the insertion instrument inserting a pedicle screw device into a pedicle of a vertebra.

The holding mechanism 5 cooperates with a distal end 90 of the control shaft 87 to shift from the releasing position (shown in FIGS. 6a-b) to the holding position (shown in FIG. 6c) and vise versa. More specifically, the holding mechanism 5 includes a driver tip housing 59 fixed to the operative (distal) end 3 of the tubular shaft 4 and a pair of actuator dogs 53 and 54, which are both coupled to the distal end 90 of the control shaft 87 via a pivot pin 57 and also coupled to the driver tip housing 59 via a fixed cam shaft pin or deployment pin 52. In this manner, the actuator dogs 53 and 54 are configured to pivot via the pivot pin 57 from the releasing position (FIGS. 6a-b) to the holding position (FIG. 6c). In the holding position, hooks 53a and 54a on respective ends of the actuator dogs 53 and 54 are positioned to engage the yoke member 12 in order to retain and hold the yoke member 12 to the holding mechanism 5.

The actuator dogs 53 and 54 hook into the yoke 12 because the camming deployment pin 52 drives the actuator dogs 53 and 54 to the deployed position with the J-shaped slots or channels in the actuator dogs 53 and 54. The cam action is caused by the deployment pin 52, which remains stationary as the actuator dogs 53 and 54 are moved by the linear motion of the deployment shaft 87 that is shifted by the resilient linkage 80, which is in turn driven by the actuator shaft 85 and lever 7.

Figure 5:
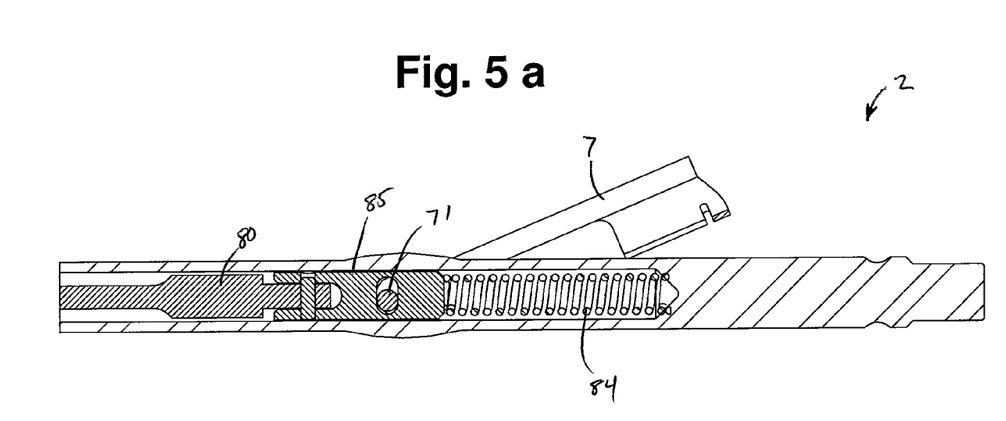
FIGS. 5a-5b are partial cross-sectional views of the positive locking actuator in the form of a lever in the unlocked position (FIG. 5a) and locked position (FIG. 5b).

Referring to FIG. 5, a partial sectional view of the proximal end 2 is shown. In FIG. 5a, the positive locking actuator 7 is shown in the unlocked position. In FIG. 5b, the actuator lever 7 is pivoted to the locked position, shifting the actuator pin 71 proximally to draw the actuator shaft 85 and superelastic linkage 80 rearward.

The actuator pin 71 is located off-center through the pivot points 75 of the actuator lever 7 (see FIG. 3), for instance approximately one and a half millimeters, which causes the actuator shaft 85 to move when the positive locking actuator 7 is pivoted to the locked position. The actuator pin 71 is disposed in a slot 89 that is elongate to allow for the arcuate motion of the actuator pin 71 during pivoting of the actuator lever 7. In one embodiment, the positive locking actuator 7 is a lever that sits flush on the exterior of the insertion instrument. The positive locking actuator 7 may be configured to be operated with the thumb of the surgeon. If the positive locking actuator 7 is depressed flush with the hollow shaft 4, the actuator shaft 85 is shifted toward the proximal direction and the superelastic rod is fully tensioned. The motion of the actuator shaft 85 in the proximal direction creates tension and elastic deformation in the resilient linkage 80.

The resilient linkage 80 is mechanically connected to the actuator shaft 85 with the proximal pin 82. The proximal pin 82 allows the resilient linkage 80 to have a simple shape in order to avoid machining of the difficult NITINOL material of the resilient linkage 80. Thus, as the actuator shaft 85 shifts in the proximal direction, the dogs of the head portion are pivoted outward to engage the pedicle screw yoke. Once the dogs are fully extended, further pivoting of the actuator level 7 causes the resilient linkage 80 to continue to tension the dogs, stretching and tensioning to act like a spring and exert an increasing holding force on the dogs.

A proximal coil spring 84 compresses as a result of the motion of the actuator shaft 85 in the proximal direction. The spring 84 serves to bias the resilient linkage 80 toward the distal end when the lever 7 is shifted to the unlocked position. However, the spring 84 is configured so that the biasing force is easily overcome by the user as the lever is pivoted. Since the linkage 80 is preferably superelastic, when the lever 7 is shifted to the unlocked position and tension on the linkage relieved, the linkage 80 returns to its original shape and is sufficiently rigid for the spring 84 to cause it to push the deployment shaft in the distal direction to retract the dogs in the head portion.

In alternative embodiments, the locking actuator 7 can be mechanically linked with a cable system, or thin wires. However, this would not provide all of the benefits of a semi-rigid superelastic rod. For instance, even if biased toward the unlocked position, a flexible cable will have difficulty pushing the holding mechanism in the distal direction, and thus may not readily unlock the holding mechanism from a pedicle screw device secured to the head of the instrument. In another embodiment, the locking actuator 7 can be mechanically linked with coiled springs.

Referring to FIG. 6a, the instrument is shown with the locking mechanism 5 in the unlocked position without an implant attached. The instrument has a tip 6 for engaging the screw head and has one or more male connection elements 62 configured for mating to female connection elements of the screw head, so that the instrument may engage and rotate the screwhead. To this end, the connection element (s) of the screw head and instrument may be lobed, polygonal, or of another non-circular shape.

In the illustrated embodiment, the male elements 62 of the driver tip 6 insert into recesses of the screw, to provide a direct mechanical engagement of the insertion instrument and the pedicle screw device. The direct mechanical engagement allows for a torque to be applied directly to the screw for drilling into the bone of the patient through rotation of the entire insertion instrument. In alternative embodiments, the driver tip 6 can have other geometries such as a cross shaped projection for a Phillips head screw arrangement, polygonal structures, or lobed structures for providing a torque to a pedicle screw. In other alternative embodiments, the implant can have projections that extend into recesses in the driver tip.

The actuator dogs 53 and 54 disposed in the driver tip housing 59 are configured to engage and hold the yoke member of a pedicle screw device with hooks 53a and 54a on respective ends of the actuator dogs 53 and 54. For the sake of simplicity, a single actuator dog 53 will be described in detail. In order to pivot from the releasing position to the holding position, the actuator dog 53 includes a pivot opening 53b sized to receive the pivot pin 57 therethrough and a cam slot 53c that cooperates with the deployment pin 52 extending through the cam slot 53c. The actuator dog 54 includes corresponding features, but will not be separately described. As a result, sliding of the control shaft 87 in the passage 14 is operative to cam or pivot the actuator dog 53. Shifting the control shaft 87 in the proximal direction 2 causes the actuator dog 53 to cam outward (FIG. 6c). This pivoting motion is achieved because the actuator dog 53 is pivotably coupled to the end 90 of the control shaft 87 via the pivot pin 57, but the deployment pin 52 is fixed to the driver tip housing 59 fixed to the rigid instrument shaft 4 and slidably received through the actuator dog cam slot 53c. Therefore, movement of the control shaft 87 in the holding direction causes a pivot end of the actuator dog to move in a similar direction, which in turn causes the cam slot 53c to engage the fixed cam pin 52, forcing the hook end 53a of the actuator dog to pivot away from the instrument axis and out of a window 150 of the housing 59.

FIGS. 6b-6c demonstrates the deployment of the actuator dogs for securing a pedicle screw device. In FIG. 6b, the actuator dogs 53 and 54 are fully retracted, and the head of the inserter is disposed in the yoke of a pedicle screw device. The connection elements 62 of the instrument are mated with the connection elements of the screw portion 11 of the pedicle screw device. Pivoting the actuator lever 7 (FIG. 5) toward the locked position begins to shift the holding mechanism 5 and control shaft 87 in the proximal direction.

As the holding mechanism 5 is shifted proximally, translation of the actuator dogs 53 and 54 against the camming deployment pin 52 causes the actuator dogs to pivot around pivot pin 57. The actuator dogs continue to pivot as the slots in the dogs cam against the deployment pin 52 until the dogs are fully deployed as in FIG. 6c.

When fully deployed as in FIG. 6c, the hooks 53a,54a on the actuator dogs are pulling upward on a lower surface of a lip 13 on the yoke portion of the pedicle screw device. This force is sufficient to rigidly hold the screw, yoke and instrument together without movement relative to any another. Advantageously, the components of the instrument can be sized and configured so that pivoting the actuator lever only part of the way from the unlocked to the locked position fully deploys the actuator dogs as in FIG. 6c, so that any additional pivoting of the lever to the locked position does not change the position of the dogs but tensions and stretches the superelastic linkage. This significantly increases the holding force on the pedicle screw device against the instrument head. In addition, the tensioning of the superelastic linkage eliminates the effect of any slack or looseness in the system caused by imprecise machining or other variation of parts, or from inherent looseness from the various moving parts.

A handle may also be provided for rotating the instrument to insert the pedicle screw device into bone. The rectangular polygonal, or other non-circular handle mounting 25 at the distal end of the instrument allows for the attachment of a drive T-handle, for instance, a quarter inch, with a quick disconnect. The quick disconnect utilizes the groove at the proximal end to quickly connect to and disconnect from the insertion instrument. The T-handle is easily snapped on and off the insertion instrument for the application of torque to the entire insertion instrument for driving implants such as pedicle screws. In alternate embodiments, the proximal end 25 could have other geometric shapes such as a hexagonal prism, triangular prism, or other polygonal prism, a lobed configuration, or other shape to allow the connection of other types of handles. Finally, the geometric relation between the holding mechanism and the hollow shaft may be designed to have a minimum profile of the insertion instrument to allow for minimally invasive surgery.

The actuator lever 7 also may be configured to confer specific advantages. As shown in FIG. 2, the actuator lever 7 may have a T-shaped groove. The T-shaped groove allows for flexing and deformation of the positive locking actuator lever 7 around the shaft of the insertion instrument. In alternative embodiments, the positive locking actuator lever 7 can have different geometries for the groove or be made from elastic materials such as NITINOL.

Figure 8:
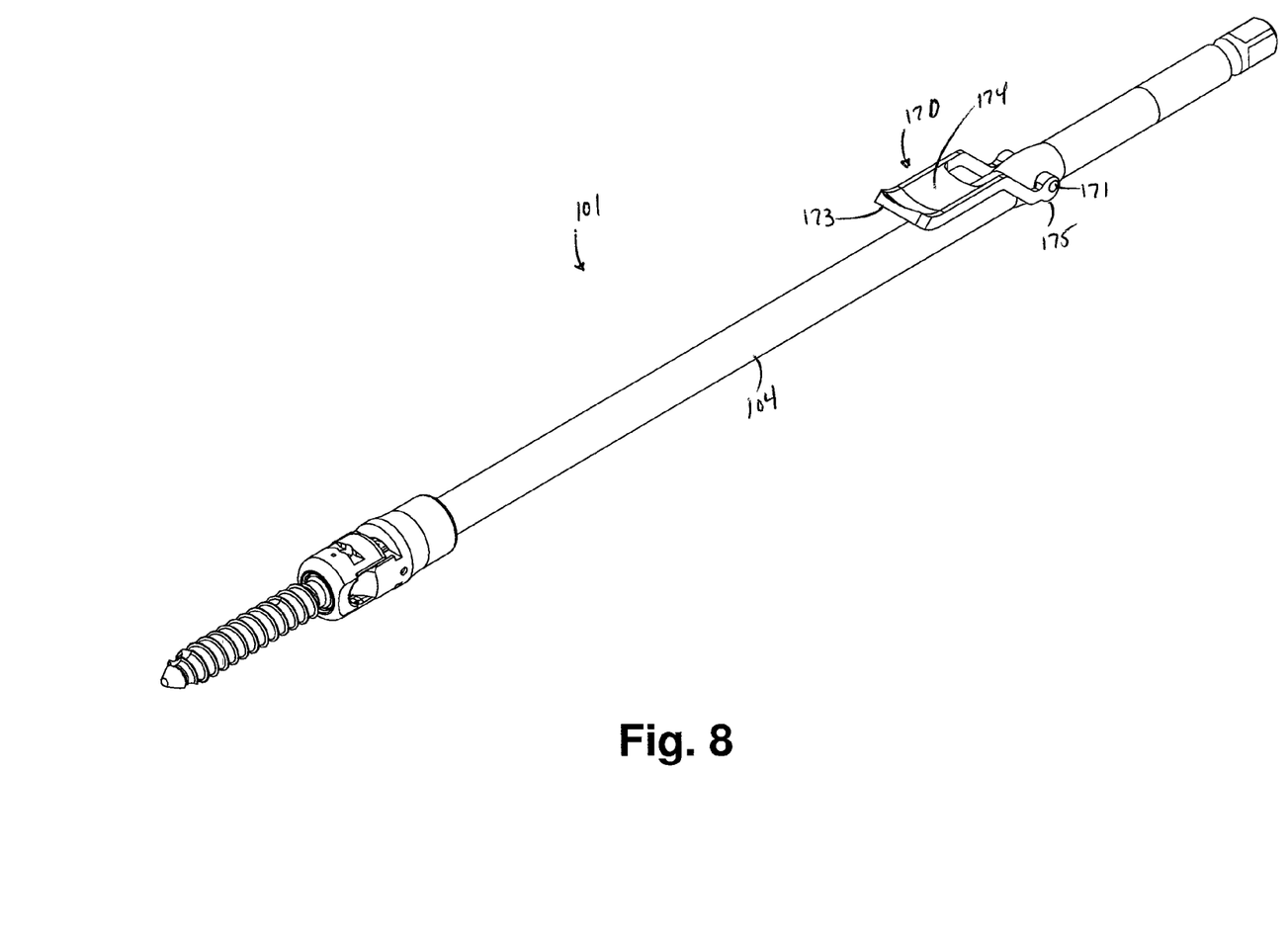
FIG. 8 is a perspective view of an alternate insertion instrument in the locked position and secured to a pedicle screw assembly.
Figure 9:
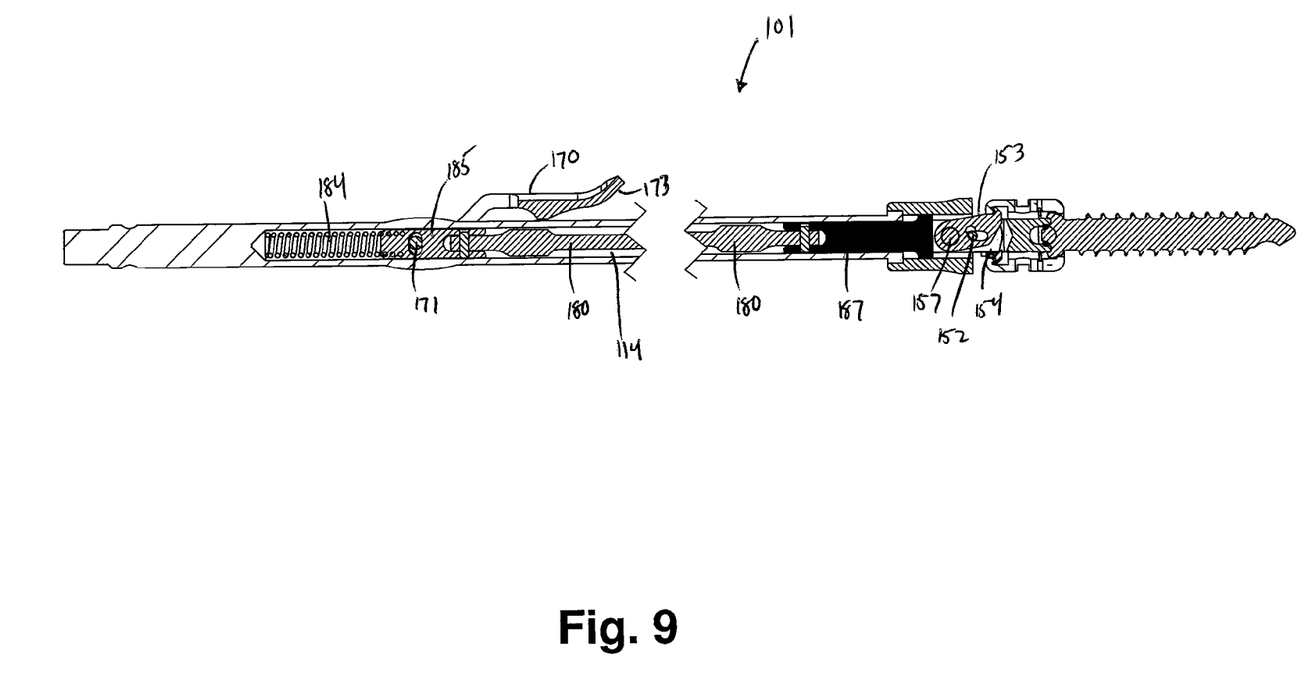
FIG. 9 is a cross-sectional view of the insertion instrument of FIG. 8
Figure 10:
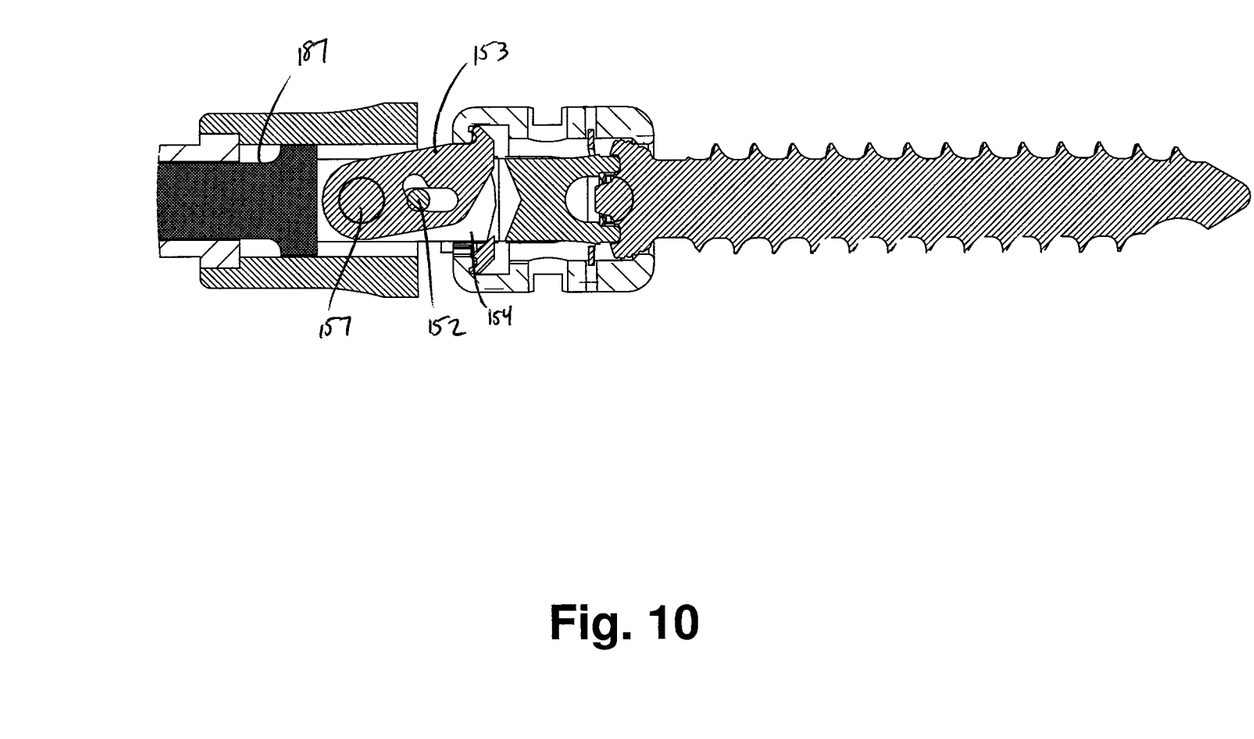
FIG. 10 is a partial cross-section of the instrument of FIG. 8 showing the holding mechanism in the locked position.

FIGS. 8-10 show an alternative embodiment of an insertion instrument 101. This alternative embodiment includes an alternative actuator lever 170 with an upwardly-directed lip 173 to more easily be manipulated by the surgeon. The lip is distanced from the main shaft of the instrument to facilitate initiation of the unlocking procedure. The actuator lever 170 may also be provided with a shallow recess 174 ergonomically designed to accommodate the surgeon's thumb as the lever is shifted and/or maintained to the locked position. The instrument of FIGS. 8-10 also includes an elongate shaft 104 has a bore 114 through which internal components of the instrument pass. At the proximal end, the pivoting actuator lever 170 is attached to the shaft 104 by hinge portions 175. An actuator pin 171 passes through the hinge portions 175 and is offset from the center of the hinges 175 so that pivoting the lever 170 about the hinges 175 shifts the actuator pin 171 proximally and distally (by generally following the circumference of the hinges 175). The pin 171 also passes through an opening 189 in an actuator shaft portion 185 that is disposed inside the bore 114 of the shaft 104. The actuator shaft 185 is biased toward the distal end of the instrument by a spring 184 also disposed in the bore 114. The actuator shaft 185 is coupled to a superelastic linkage 180, which is in turn coupled to a control shaft 187 that controls the deployment of actuator dogs 153 and 154 configured to grasp and hold the yoke of a pedicle screw device. Pivoting of the actuator lever 170 shifts the off-center actuator pin 171, causing linear travel of the actuator shaft 85, superelastic linkage 180, and control shaft 187 through the bore 114 of the shaft portion 104. The actuator dogs 153 and 154 are pivotably coupled to the control shaft 187. A pivot pin 157 fixes one end of the control shaft 187, and a deployment pin 152 fixed to the shaft 104 and disposed through elongate openings 188 of the control shaft 187. The control shaft 187 is able to travel linearly through the bore 114 of the shaft 104 despite the fixed deployment pin 152 disposed therethrough, because of the elongate shape of the opening opening 188. As the control shaft 187 and the actuator dogs 153 and 154 connected thereto via the pivot pin 157 travel with respect to the deployment pin 152, the deployment pin 152 cams against the actuator dogs 153 and 153, as explained below, to pivot the actuator dogs outward and deploy the ends thereof outward through openings 150 through the housing 159 of the head portion.

The insertion instruments described herein can be made from any suitable, structurally strong material. The structural support portion and other components, such as the projections, are constructed of suitable materials which are compatible with the uses and environments into which the device will be utilized. Preferably, the insertion instrument, especially the exterior component, is constructed of metallic materials such as stainless steel. Alternatively, the exterior components can be made of other metal alloys such as titanium. Preferably, the interior components will be made of NITINOL or another superelastic alloy to provide a resilient material capable of creating a tensile force. Alternatively, any hardened steel suitable for acting as a spring can also be used such as stainless steel.

In some embodiments, the insertion instrument can be made from non-conductive material such as various plastics, such as polyetheretherketone (PEEK), in order to prevent any conduction of electricity. In some other embodiments, the insertion instrument can be made from ceramics that provide non-conductive characteristics. Finally, a composite of the previously discussed materials can be used that combine the properties of the said materials, i.e. conductive metals and non-conductive materials.

It is intended for the following claims to cover these and any other departures from the disclosed embodiment which fall within the true spirit of the invention.

What is claimed is:

1. A system for securing a spinal rod, the system including:
   a coupling device configured to receive an elongate member and secure the elongate member to a bone, the coupling device having a hollow space for receiving the elongate member and side walls having interior surfaces adjacent the hollow space; and
   an insertion instrument configured to engage the coupling device and for securing the coupling device to a bone, the insertion instrument further comprising:
   a head portion having deployable and retractable engagement members for engaging the interior surfaces of the coupling device;

a rigid hollow shaft portion having a bore therein, the shaft portion fixed to the head portion;

a pivotable actuator member configured to pivot between a first predetermined position and a second predetermined position; and a rigid or semi-rigid link member coupled to the engagement members and the actuator member and disposed between the actuator member and at least one of the engagement members for deploying the engagement members in response to pivoting of the actuator member;

the link member comprising a generally rod-shaped superelastic metal alloy portion having a central axis, a length, and a diameter, the length greater than the diameter;

the link member shiftable through the bore and along the central axis without rotation by operation of the actuator member in order to push or pull the engagement members between deployed and retracted positions;

wherein the engagement members are fully retracted when the actuator member is pivoted to the second position and fully deployed when the actuator member is pivoted between the first position and second position; and wherein pivoting the actuator member to the first position tensions and stretches the link member along the central axis after the engagement members have been fully deployed in order to reduce slack between two or more components of the insertion instrument operatively disposed between the actuator member and the engagement members and to produce at least about 100 pounds of force to hold the coupling device when the engagement members are deployed into engagement with the interior surfaces of the coupling device, the strain on the superelastic portion not exceeding 0.8% when the actuator member is in the first position.

2. The system of claim 1, wherein the engagement members are pivotable in response to shifting of the link member.

3. The system of claim 1, wherein pivoting of the actuator to the first predetermined position shifts the link member away from the head portion to deploy the engagement members and pivoting of the actuator to the second predetermined position shifts the link member toward the head portion to retract the engagement members.

4. The system of claim 1, wherein the engagement members include a slot portion configured to cam against a fixed pin as the engagement members are shifted by the superelastic portion of the link member.

5. The system of claim 1 wherein the superelastic link member shifts linearly in response to pivoting of the actuator member and becomes tensioned and stretched as the approaches the first predetermined position after the engagement members have been fully deployed.

6. The system of claim 5 wherein the superelastic link member comprises NITINOL.

* * * * *